United States Patent
Coffin et al.

(10) Patent No.: US 6,248,320 B1
(45) Date of Patent: Jun. 19, 2001

(54) HSV STRAIN LACKING FUNCTIONAL ICP27 AND ICP34.5 GENES

(75) Inventors: Robert Stuart Coffin; David Seymour Latchman, both of London; Alasdair Roderick Maclean; Suzanne Moira Brown, both of Glasgow, all of (GB)

(73) Assignees: University College London, London; The University Court of the University of Glasgow, Glasgow, both of (GB)

( * ) Notice: Subject to any disclaimer, the term of this patent is extended or adjusted under 35 U.S.C. 154(b) by 0 days.

(21) Appl. No.: 09/230,479

(22) PCT Filed: Jul. 25, 1997

(86) PCT No.: PCT/GB97/02017

§ 371 Date: Jun. 10, 1999

§ 102(e) Date: Jun. 10, 1999

(87) PCT Pub. No.: WO98/04726

PCT Pub. Date: Feb. 5, 1998

(30) Foreign Application Priority Data

Jul. 26, 1996 (GB) .................................................. 9615794

(51) Int. Cl.[7] .............................. A01N 63/00; C12N 7/00; C12N 7/04; C12N 15/00

(52) U.S. Cl. ..................... 424/93.2; 424/93.3; 435/235.1; 435/236; 435/320.1

(58) Field of Search ........................ 424/93.6; 435/320.1; 514/44

(56) References Cited

U.S. PATENT DOCUMENTS

| | | |
|---|---|---|
| 4,859,587 | 8/1989 | Roizman . |
| 5,328,688 | * 7/1994 | Roizman ........................... 424/205.1 |
| 5,585,096 | 12/1996 | Martuza et al. . |
| 5,658,724 | 8/1997 | DeLuca . |

FOREIGN PATENT DOCUMENTS

| | | |
|---|---|---|
| 0 453 242 | 10/1991 | (EP) . |
| 0 487 611 | 6/1992 | (EP) . |
| 92 04050 | 3/1992 | (WO) . |
| WO 92/04050 | 3/1992 | (WO) . |
| WO 92/13943 | 8/1992 | (WO) . |
| WO 93/19591 | 10/1993 | (WO) . |
| WO 94/03207 | 2/1994 | (WO) . |
| WO 96/00007 | 1/1996 | (WO) . |
| 96 04395 | 2/1996 | (WO) . |
| WO 96/03997 | 2/1996 | (WO) . |
| WO 96/04394 | 2/1996 | (WO) . |
| WO 96/04395 | 2/1996 | (WO) . |
| WO 97/10349 | 3/1997 | (WO) . |
| WO 98/15637 | 4/1998 | (WO) . |

OTHER PUBLICATIONS

Jain KR, "Vascular and interstitial barriers to delivery of therapeutic agents in tumors". Cancer and Metastasis Review 9; pp. 253–266, 1990.*

Orkin et al., Report and recommendations of the panel to assess the NIH investment in research on gene therapy. pp. 1–20, Dec. 1995.*

Breakefield et al., "Herpes simplex virus and gene delivery to neurons". The New Biologist, vol. 3. No. 3: pp. 203–218, Mar. 1991.*

Samaniego et al., Functional interactions between Herpes Simplex Virus immediate–early proteins during infection: Gene expression as a consequence of ICP27 and different domains of ICP4. Journal of Virology vol. 69, No. 9 : pp. 5705–5715, Sep. 1995.*

Smibert et al., "Herpes Simplex Virus VP16 forms a complex with the virion host shutoff protein vhs". Journal of Virology vol. 68, No. 4: pp. 2339–2346, Apr. 1994.*

Verma et al., "Gene therapy–promises, problems, and prospects". Nature vol. 389 : pp. 239–242, Sep. 1997.*

Anderson WF, "Human gene therapy". Nature vol. 392: pp. 25–30, Apr. 1998.*

Thompson et al, "DNA Sequence and RNA Transcription through a Site of Recombination in a Non–neurovirulent Herpes Simplex Virus Intertypic Recombinant", Virus Genes 1(3):275–286 (1988).

Thompson and Stevens, "Biological Characterization of a Herpes Simplex Virus Intertypic Recombinant Which Is Completely and Specifically Non–Neurovirulent", Virology 131:171–179 (1983).

Ace et al, "Construction and Characterization of a Herpes Simplex Virus Type 1 Mutant Unable To Transinduce Immediate–Early Gene Expression", Journal of Virology 63(5):2260–2269 (1989).

Chiocca et al, "Transfer and Expression of the *lacZ* Gene in Rat Brain Neurons Mediated by Herpes Simplex Virus Mutants", The New Biologist 2(8):739–746 (1990).

Chou et al, "Differential Response of Human Cells to Deletions and Stop Codons in the $_{\gamma 1}34.5$ Gene of Herpes Simplex Virus", Journal of Virology 68(12):8304–8311 (1994).

Chou and Roizman, "The $_{\gamma 1}34.5$ gene of herpes simplex virus 1 precludes neuroblastoma cells from triggering total shutoff of protein synthesis characteristics of programed cell death in neuronal cells", Proc. Natl. Acad. Sci. USA 89:3266–3270 (1992).

(List continued on next page.)

Primary Examiner—Karen M. Hauda
Assistant Examiner—Shin-Lin Chen
(74) Attorney, Agent, or Firm—Nixon & Vanderhye P.C.

(57) ABSTRACT

The present invention provides a herpes simplex virus strain which lacks a functional ICP34.5 gene and a functional ICP27 gene. It also provides the use of a herpes simplex virus strain which lacks a functional ICP34.5 gene and a functional ICP27 gene in the treatment of disorders of, or injuries to, the nervous system of a mammal.

30 Claims, No Drawings

OTHER PUBLICATIONS

Coffin and Latchman, Herpes Simplex virus–based vectors. In Latchman, DS (ed.), Genetic manipulation of the nervous system, Academic Press: London, pp. 99–114 (1996).

DeLuca et al, "Isolation and Characterization of Deletion Mutants of Herpes Simplex Virus Type 1 in the Gene Encoding Immediate–Early Regulatory Protein ICP4", Journal of Virology 56(2):558–570 (1985).

Dobson et al, "A Latent, Nonpathogenic HSV–1–Derived Vector Stably Expresses β–Galactosidase in Mouse Neurons", Neuron 5:353–360 (1990).

Lokensgard et al, "Long–Term Promoter Activity during Herpes Simplex Virus Latency", Journal of Virology 68(11):7148–7158 (1994).

MacLean et al, "Herpes simplex virus type 1 deletion variants 1714 and 1716 pinpoint neurovirulence–related sequences in Glasgow strain 17+ between immediate early gene 1 and the a sequence", Journal of General Virology 72:631–639 (1991).

McFarlane et al, "Hexamethylene bisacetamide stimulates herpes simplex virus immediate early gene expression in the absence of trans–induction by Vmw65", Journal of General Virology 73:285–292 (1992).

Hardy and Sandri–Goldin, "Herpes Simplex Virus Host Cell Splicing, and Regulatory Protein ICP27 Is Required for This Effect", Journal of Virology 68(12):7790–7799 (1994).

Rice and Knipe, "Genetic Evidence for Two Distinct Trans-activation Functions of the Herpes Simplex Virus α Protein ICP27", 64:1704–1715 (1990).

Samaniego et al, "Functional Interactions between Herpes Simplex Virus Immediate–Early Proteins during Infection: Gene Expression as a Consequence of ICP27 and Different Domains of ICP4", Journal of Virology 69(9):5705–5715 (1995).

Sekulovich et al, "The Herpes Simplex Virus Type 1 α Protein ICP27 Can Act as a trans –Repressor or a trans— Activator in Combination with ICP4 and ICP0", Journal of Virology 62(12):4510–4522 (1988).

Smith et al, "Evidence That The Herpes Simplex Virus Immediate Early Protein ICP27 Acts Post–Transcriptionally during Infection to Regulate Gene Expression", Virology186:74–86 (1992).

Coffin et al, "Gene delivery to the heart in vivo and to cardiac myocytes and vascular smooth muscle cells in vitro using herpes virus vectors", Gene Therapy 3:560–566 (1996).

Coffin et al, "Gene delivery to the central and peripheral nervous systems of mice using HSV1 ICP34.5 deletion mutant vectors", Gene Therapy 3:886–891 (1996).

Mineta et al, "Attenuated multi–mutated herpes simplex virus–1 for the treatment of malignant gliomas", Nature Medicine 1(9):938–943 (1995).

Chou et al, "Mapping of Herpes Simplex Virus–1 Neurovirulence to ∓134.5, A Gene Nonessential For Growth In Culture", Science 250(4985):1262–1266 (1990).

* cited by examiner

HSV STRAIN LACKING FUNCTIONAL ICP27 AND ICP34.5 GENES

FIELD OF THE INVENTION

The present invention relates to mutant herpes simplex virus strains which have inactivating mutations rendering them non-pathogenic. It also relates to the use of such mutant HSV strains in gene therapy and in methods of assaying for gene function.

BACKGROUND TO THE INVENTION

Herpes simplex virus (HSV) has often been suggested as a suitable vector for the nervous system due to its neurotrophic lifestyle and its ability to remain in neurons for the lifetime of the cell. However wild type HSV is highly pathogenic and must like most viral vectors be disabled in some way. The pathogenic effects of HSV result from lytic infection with the virus and therefore the use of HSV as a vector requires the development of strains carrying mutations that disrupt the lytic cycle whilst allowing the establishment of asymptomatic latent infections. HSV vectors have previously been produced and tested in vivo by the deletion of the essential immediate early (IE) gene ICP4 (Dobson et al., 1990 and Chiocca et al., 1990), which must be complemented for growth in culture. ICP4 is required for transcriptional activation of the viral early and late genes in lytic infection. Thus, a virus lacking this gene can readily establish latent infection of cells but cannot grow lytically.

Mutations have also been made in non-essential genes such as the IE gene ICP0, the IE gene ICP6, tyrosine kinase (TK), US5 or VMW65, all of which are required for full pathogenicity in vivo but are dispensable for growth in culture (reviewed by Coffin and Latchman, 1996). These types of mutation provide the added advantage that the deletion need not be complemented for growth in culture which has been shown previously to occasionally result in reversion of the non-pathogenic phenotype to a wild-type phenotype by homologous recombination between the virus and the complementing sequences in the cell-line during growth. However in each of these cases, mutation of the non-essential gene does not completely prevent virus replication since high titre inoculation will overcome the block to replication in vivo.

We have tested, as vectors, HSV mutant strains deleted for the ICP34.5 gene—the so-called neurovirulence factor—which is absolutely required for neurovirulence in vivo, but is again unnecessary for growth in culture (Chou et al., 1990). Mutations in ICP34.5 provide a subtle mechanism by which HSV can be disabled. ICP34.5 is thought to prevent the usual host response to a productive infection in neurons, which results (in the absence of ICP34.5) in cell death and thus the limitation of the infection to initially infected cells. ICP34.5 is thought to over-ride this response and allow full lytic replication to occur. Thus in the absence of ICP34.5, if a disabled virus were ever to re-establish a productive infection for whatever reason, the ICP34.5 mutation would ensure that the protective host response limited virus replication to a small number of cells.

To test the possibility that ICP34.5 deleted herpes viruses might be developed as vectors for the nervous system, we inserted a lacZ construct into a non-essential gene (UL43) of the HSV1 ICP34.5 deletion mutant strain 1716, and inoculated mice via the footpad route (for delivery to dorsal root ganglia (DRGs)) and intracranially. LacZ activity (as assayed by X-gal staining), could be seen in a limited number of cells in the DRGs and brain respectively (unpublished observations). These results indicate that HSV strains carrying inactivating mutations in ICP34.5 are suitable for use as gene-delivery vectors. ICP34.5 deletion mutants could thus provide the basis for further development as novel and safe gene-delivery vectors for the nervous system.

However, it is unlikely that viruses carrying a single defect will be considered safe enough for eventual human use. Added safety and the possibility of higher titre inoculation might be achieved by the deletion of an essential IE gene providing an absolute block to replication (and which must thus be complemented in culture), together with ICP34.5. Previously HSV vectors disabled by removal of essential IE genes and used in vivo have been deleted for ICP4 as this single deletion absolutely prevents replication and provides the greatest reduction in the levels of other HSV gene products. However the other IE genes (ICP0, 27, 22 and 47) are still produced and of these the essential ICP27 is highly cytotoxic probably due to its secondary role of preventing the splicing of pre-mRNAs in favour of translation from the mainly unspliced herpes RNAs. We therefore speculated that removal of ICP27 (to be complemented in culture) might produce a safer and less cytotoxic vector system when combined with deletions in ICP34.5. While a number of ICP27 deletion mutant viruses have been produced and used, for example, to study herpes gene regulation in vitro and the effects of ICP27 on the host cell (Reef Hardy and Sandri-Goldin, 1994 and Rice and Knipe, 1990), none has reportedly been tested as a vector for gene delivery to the nervous system in vivo. Furthermore, none of the ICP27 deletion mutant viruses carry a mutation in ICP34.5.

SUMMARY OF THE INVENTION

This invention relates to mutant herpes simplex virus strains which have been disabled for use as gene delivery vectors by the functional inactivation of both ICP34.5 and ICP27. Such HSV strains can be used, for example, for delivering therapeutic genes in methods of treatment of diseases of, or injuries to, the nervous system, including Parkinson's disease, spinal injury or strokes, or diseases of the eye, heart or skeletal muscles, or malignancies. The present invention also relates to methods for studying the function of genes in mammalian cells, for example in identifying genes complementing cellular dysfunctions, or studying the effect of expressing mutant genes in wild-type or mutant mammalian cells. The methods of the present invention may be used in particular for the functional study of genes implicated in disease.

We have now surprisingly found that HSV strains carrying inactivating mutations in both ICP34.5 and ICP27 genes exhibit greatly improved levels of expression of heterologous genes compared to virus strains carrying mutations in ICP34.5 alone. These doubly-mutated strains are also safer than strains carrying mutations in ICP27 alone. We have also shown that an additional inactivating mutation in ICP4 and an inactivating mutation in VMW65, which abolishes its transcriptional-activation activity, reduces further the toxicity of the viral strains of the invention. Thus, the viral strains of the present invention are not only safer than previous strains, but also offers high levels of expression of heterologous genes.

Accordingly the present invention provides a herpes simplex virus strain which lacks a functional ICP34.5 gene and a functional ICP27 gene. Preferably, the HSV strain of the invention further lacks a functional form of other IE genes, more preferably the IE gene ICP4. Inactivation of the essential IE ICP4 gene prevents viral replication and provides the greatest reduction in the levels of other HSV gene products. The HSV strain of the invention preferably also lacks a functional vhs gene and/or a functional VMW65 gene due to a mutation in said VMW65 gene that abolishes its transcriptional-activation activity. In a particulary preferred embodiment of the present invention, the HSV strain lacks a functional ICP34.5 gene, a functional ICP27 gene, a functional ICP4 gene and a functional VMW65 gene due to a mutation in said VMW65 gene which abolishes its transcriptional-activation activity.

The invention further provides an HSV strain of the invention which carries a heterologous gene. The term heterologous gene is intended to embrace any gene not found in the HSV genome. The heterologous gene may be any allelic variant of a wild-type gene, or it may be a mutant gene. Heterologous genes are preferably operably linked to a control sequence permitting expression of said heterologous gene in mammalian cells, preferably cells of the central or peripheral nervous system, or cells of the eye, heart or skeletal muscle, more preferably cells of the central or peripheral nervous system. The HSV strain of the invention may thus be used to deliver a heterologous gene to a mammalian cell where it will be expressed. Such vectors are useful in a variety of applications, for example, in gene therapy, or in vitro assay methods or for the study of HSV gene regulation.

The heterologous gene preferably encodes a polypeptide of therapeutic use, including polypeptides that are cytotoxic or capable of converting a precursor prodrug into a cytotoxic compound.

The invention further provides herpes simplex virus strains of the invention, carrying a heterologous gene, for use in the treatment of humans and animals. For example, such HSV strains may be used in the treatment of diseases of, or injury to, the nervous system, including Parkinson's disease, spinal injury or strokes or disease of the eye, heart or skeletal muscle, or malignancies.

The HSV strains of the present invention may also be used in methods for studying the function of genes in mammalian cells, for example in identifying genes complementing cellular dysfunctions, or studying the effect of expressing mutant genes in wild-type or mutant mammalian cells. The methods of the present invention may be used in particular for the functional study of genes implicated in disease.

The invention also provides a method for producing a herpes simplex virus of the present invention, said method comprising modifying the ICP34.5 and ICP27 genes of a herpes simplex virus so as to inactivate them functionally. The method of the invention may further comprise modifying a second IE gene, preferably the ICP4 gene, so as to inactivate it functionally, and/or modifying the VMW65 gene so to inactivate functionally its transcriptional-activation activity.

DETAILED DESCRIPTION OF THE INVENTION

A. Viral Strains

The HSV strains of the invention may be derived from, for example, HSV-1 or HSV-2 strains, or derivatives thereof, preferably HSV-1. Derivatives include inter-type recombinants containing DNA from HSV-1 and HSV-2 strains. Derivatives preferably have at least 80% sequence homology to either the HSV-1 or HSV-2 genomes, more preferably at least 90%, even more preferably 95%. Other derivatives which may be used to obtain the HSV strains of the, present invention include strains that already have mutations in either ICP34.5 or ICP27, for example strain 1716 (MacLean et al., 1991), strains R3616 and R4009 (Chou and Roizman, 1992) and R930 (Chou et al., 1994) all of which have mutations in ICP34.5, and d27-1 (Rice and Knipe, 1990) which has a deletion in ICP27. Viral strains that have deletions in other HSV genes may also be conveniently used, for example strain dl 20 which has a deletion in ICP4 (DeLuca et al., 1985) or strain d92 which has deletions in both ICP27 and ICP4 (Samaniego et al., 1995). Use of these strains will reduce the number of steps required to produce the mutant HSV strains of the present invention.

The terminology used in describing the various HSV genes is as found in Coffin and Latchman, 1996.

B. Complementing Cell Lines

The virus of the invention is propagated on a cell line expressing ICP27, for example V27 cells (Rice and Knipe, 1990), 2—2 cells (Smith et al., 1992) or B130/2 cells (see Example 1), preferably B130/2 cells.

ICP27-expressing cell lines can be produced by co-transfecting mammalian cells, for example the Vero or BHK cells, with a vector, preferably a plasmid vector, comprising a functional HSV ICP27 gene capable of being expressed in said cells, and a vector, preferably a plasmid vector, encoding a selectable marker, for example neomycin resistance. Clones possessing the selectable marker are then screened further to determine which clones also express functional ICP27, for example on the basis of their ability to support the growth of ICP27⁻HSV strains, using methods known to those skilled in the art (for example as described in Rice and Knipe, 1990).

Cell lines which do not allow reversion of an ICP27⁻ mutant HSV strain to a strain with functional ICP27 are produced as described above, ensuring that the vector comprising a functional ICP27 gene does not contain sequences that overlap with (i.e. are homologous to) sequences remaining in the ICP27⁻mutant virus.

Where HSV strains of the invention comprise inactivating modifications in other essential genes, for example ICP4, complementing cell lines will further comprise a functional HSV gene which complements the modified essential gene in the same manner as described for ICP27. For example in the case of HSV strains comprising mutations in both ICP27 and ICP4, a cell line expressing both ICP27 and ICP4 is used (such as E26 cells (Samaniego et al., 1995) or B4/27 cells (see Example 3), preferably B4/27 cells).

Cells expressing ICP27 and ICP4 are produced by transfecting mammalian cells, for example Vero or BHK cells, with similar vectors as those used for production of ICP27-expressing cell lines, i.e. expressing ICP27 and a selectable marker, together with a third vector, preferably a plasmid vector, comprising a functional ICP4 gene capable of being expressed in said cells. Clones possessing the selectable marker are then screened further to determine which clones also express ICP27 and ICP4, for example on the basis of their ability to support growth of ICP27 and ICP4 mutant HSV strains, again using methods known to those skilled in the art (for example as described in Samaniego et al., 1995).

C. Methods of Mutation.

The ICP34.5 and ICP27 genes may be rendered functionally inactive by several techniques well known in the art. For example, they may be rendered functionally inactive by deletions, substitutions or insertions, preferably by deletion. Deletions may remove portions of the genes or the entire gene. Inserted sequences may include the heterologous genes described below.

Mutations are made in the HSV strains by homologous recombination methods well known to those skilled in the art. For example, HSV genomic DNA is transfected together with a vector, preferably a plasmid vector, comprising the mutated sequence flanked by homologous HSV sequences. The mutated sequence may comprise deletions, insertions or substitutions, all of which may be constructed by routine techniques. Insertions may include selectable marker genes, for example lacZ, for screening recombinant viruses by, for example, β-galactosidase activity.

Mutations may also be made in other HSV genes, for example IE genes such as ICP0, ICP4, ICP6, ICP22 or ICP47, preferably ICP4, VMW65 or vhs. In the case of the VMW65 gene, the entire gene is not deleted since it encodes an essential structural protein, but a small inactivating insertion is made which abolishes the ability of VMW65 to activate transcriptionally IE genes (Ace et al., 1989).

D. Heterologous Genes

The mutant HSV strains of the invention may be modified to carry a heterologous gene, that is to say a gene other than one present in the HSV genome. The term "gene" is intended to cover at least sequences which are capable of being transcribed, optionally with some or all of 5' and/or 3' transcribed but untranslated flanking sequences naturally associated with the translated coding sequence. It may optionally further include the associated transcriptional and/or translational control sequences normally associated with the transcribed sequences. The heterologous gene may be inserted into the HSV genome at any location provided that the virus can still be propagated, which may require the use of a cell line carrying another HSV essential gene (as described in B.) if the heterologous gene is inserted into an essential gene. For example, if the heterologous gene is inserted into the ICP4 gene of the mutant HSV strain, then a cell-line expressing both ICP27 and ICP4 would be needed. The heterologous gene is preferably inserted into the region of the ICP27 mutation as in the unlikely event that the mutation is repaired by recombination with a wild-type virus, the repair would remove the inserted heterologous gene.

The heterologous gene may be inserted into the HSV genome by homologous recombination of HSV strains with, for example, plasmid vectors carrying the heterologous gene flanked by HSV sequences. The heterologous gene may be introduced into a suitable plasmid vector comprising HSV sequences using cloning techniques well-known in the art.

The transcribed sequence of the heterologous gene is preferably operably linked to a control sequence permitting expression of the heterologous gene in mammalian cells, preferably cells of the central and nervous system. The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequence.

The control sequence comprises a promoter allowing expression of the heterologous gene and a signal for termination of transcription. The promoter is selected from promoters which are functional in mammalian, preferably human, cells. The promoter may be derived from promoter sequences of eukaryotic genes. For example, it may be a promoter derived from the genome of a cell in which expression of the heterologous gene is to occur, preferably a cell of the mammalian central or peripheral nervous system. With respect to eukaryotic promoters, they may be promoters that function in a ubiquitous manner (such as promoters of α-actin, tubulin) or, alternatively, a tissue-specific manner (such as promoters of the genes for pyruvate kinase). They may also be promoters that respond to specific stimuli, for example promoters that bind steroid hormone receptors. Viral promoters may also be used, for example the Moloney murine leukaemia virus long terminal repeat (MMLV LTR) promoter. The HSV LAT promoter, and promoters containing elements of the LAT promoter region, may be especially preferred because there is the possibility of achieving long-term expression of heterologous genes during latency.

In addition, any of these promoters may be modified by the addition of further regulatory sequences, for example enhancer sequences. Chimeric promoters may also be used comprising sequence elements from two or more different promoters described above, for example an MMLV LTR/LAT fusion promoter (Lokensgard et al., 1994) or promoters comprising elements of the LAT region.

The heterologous gene may encode, for example, proteins involved in the regulation of cell division, for example mitogenic growth factors including neurotrophic growth factors (such as brain-derived neurotrophic factor, glial cell derived neurotrophic factor, NGF, NT3, NT4 and NT5, GAP43 and), cytokines (such as α-,β- or γ-interferon, interleukins including IL-1, IL-2, tumour necrosis factor, or insulin-like growth factors I or II), protein kinases (such as MAP kinase), protein phosphatases and cellular receptors for any of the above. The heterologous gene may also encode enzymes involved in cellular metabolic pathways, for example enzymes involved in amino acid biosynthesis or degradation (such as tyrosine hydroxylase), purine or pyrimidine biosynthesis or degradation, and the biosynthesis or degradation of neurotransmitters, such as dopamine, or protein involved in the regulation of such pathways, for example protein kinases and phosphatases. The heterologous gene may also encode transcription factors or proteins involved in their regulation, for example members of the Brn3 family (including Brn-3*a*, Brn-3*b* and Brn-3*c*) or pocket proteins of the Rb family such as Rb or p107, membrane proteins (such as rhodopsin), structural proteins (such as dystrophin) or heat shock proteins such as hsp27, hsp65, hsp70 and hsp90.

Preferably, the heterologous gene encodes a polypeptide of therapeutic use. For example, of the proteins described above, tyrosine hydroxylase can be used in the treatment of Parkinson's disease, rhodopsin can be used in the treatment of eye disorders, dystrophin may be used to treat muscular dystrophy, and heat shock proteins can be used to treat disorders of the heart. Polypeptides of therapeutic use may also include cytotoxic polypeptides such as ricin, or enzymes capable of converting a precursor prodrug into a cytotoxic compound for use in, for example, methods of virus-directed enzyme prodrug therapy or gene-directed enzyme prodrug therapy. In the latter case, it may be desirable to ensure that the enzyme has a suitable signal sequence for directing it to the cell surface, preferably a signal sequence that allows the enzyme to be exposed on the exterior of the cell surface whilst remaining anchored to cell membrane. Suitable enzymes include bacterial nitroreductase such as *E. coli* nitroreductase as disclosed in WO93/08288 or carboxypeptidase, especially carboxypeptidase CPG2 as disclosed in WO88/07378. Other enzymes may be found by reference to EP-A-415731. Suitable prodrugs include nitrogen mustard prodrugs and other compounds such as those described in WO88/07378, WO89/10140, WO90/02729 and WO93/08288 which are incorporated herein by reference.

E. Administration

The mutant HSV strains of the present invention may thus be used to deliver therapeutic genes to a human or animal in need of treatment. Delivery of therapeutic genes using the mutant HSV strains of the invention may be used to treat for example, Parkinson's disease, disorders of the nervous system, spinal injury, strokes or malignancies, for example gliomas.

One method for administered gene therapy involves inserting the therapeutic gene into the genome of the mutant HSV strain of the invention, as described above, and then combining the resultant recombinant virus with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intravenous, subcutaneous, intraocular or transdermal administration.

The pharmaceutical composition is administered in such a way that the mutated virus containing the therapeutic gene for gene therapy, can be incorporated into cells at an appropriate area. For example, when the target of gene therapy is the central or peripheral nervous system, the composition could be administered in an area where synaptic terminals are located so that the virus can be taken up into the terminals and transported in a retrograde manner up the axon into the axonal cell bodies via retrograde axonal transport. The pharmaceutical composition is typically administered to the brain by stereotaxic inoculation. When the pharmaceutical composition is administered to the eye, sub-retinal injection is typically the technique used.

The amount of virus administered is in the range of from $10^4$ to $10^8$ pfu, preferably from $10^5$ to $10^7$ pfu, more preferably about $10^6$ pfu. When injected, typically 1–2 $\mu$l of virus in a pharmaceutically acceptable suitable carrier or diluent is administered.

The routes of administration and dosages described are intended only as a guide since a skilled practitioner will be able to determine readily the optimum route of administration and dosage for any particular patient and condition.

F. Assay Methodologies

The mutant HSV strains of the invention can also be used in methods of scientific research. Thus, a further aspect of the present invention relates to methods of assaying gene function in mammalian cells, either in vitro or in vivo. The function of a heterologous gene could be determined by a method comprising:

(a) introducing said heterologous gene into a mutant HSV strain of the invention;

(b) introducing the resulting HSV strain into a mammalian cell line; and (c) determining the effect of expression of said heterologous gene in said mammalian cell-line.

For example, the cell-line may have a temperature-sensitive defect in cell division. When an HSV strain comprising a heterologous gene according to the invention is introduced into the defective cell-line and the cell-line grown at the restrictive temperature, a skilled person will easily be able to determine whether the heterologous gene can complement the defect in cell division. Similarly, other known techniques can be applied to determine if expression of the heterologous gene can correct an observable mutant phenotype in the mammalian cell-line.

This procedure can also be used to carry out systematic mutagenesis of a heterologous gene to ascertain which regions of the protein encoded by the gene are involved in restoring the mutant phenotype.

This method can also be used in animals, for example mice, carrying so-called "gene knock-outs". A wild-type heterologous gene can be introduced into the animal using a mutant HSV strain of the invention and the effect on the animal determined using various behavioural, histochemical or biochemical assays known in the art. Alternatively, a mutant heterologous gene can be introduced into either a wild-type or "gene knock-out" animal to determine if disease-associated pathology is induced. An example of this is the use of genes encoding prions to induce Creutzfeld-Jacob and other prion-type diseases in the central nervous system of rodents. Other disease models may include those for Alzheimer's disease, motor neurone disease or Parkinson's disease.

Thus, the methods of the present invention may be used in particular for the functional study of genes implicated in disease.

The invention will be described with reference to the following Examples, which are intended to be illustrative only and not limiting.

EXAMPLES

Example 1

Production of Mutant Viruses

Viruses

ICP27 deletion mutants were produced by homologous recombination of plasmid pΔMNlacZ with wild-type HSV strain 17+ DNA and also with strain 1716 DNA (MacLean et al., 1991) to generate viruses zΔMN:+ and zΔMN:16 deleted for ICP27 and ICP27 together with ICP34.5 respectively, and each having a lacZ gene driven by the moloney murine leukaemia virus long terminal repeat (MMLV LTR) promoter (Shinnick et al., 1981) replacing the entire coding sequence of ICP27 (and also non-essential genes UL55 and 56). Nucleotide numbers refer to the HSV-1 strain 17+sequence (Genbank no. HE1CG).

Viruses were generated and stocks prepared by growth on ICP27 complementing BHK cell line B130/2 described below. pΔMnlacz was produced by deleting a NotI/XmnI fragment from the EcoRI B fragment of the HSV-1 genome cloned into pACYC184 (NBL), to leave a fragment which includes the gene for ICP27 and flanking sequences (HSV-1 strain 17+ nts 11095–118439). A pair of MluI fragments encoding the entire ICP27 coding sequence together with the non-essential genes UL55 and 56 (nts 113273–116869) were then removed by digestion with MluI and religation (to give plasmid pΔMN) and replaced by the insertion of an MMLV LTR/lacZ cassette into the MluI site as an NheI/PstI fragment from pJ4lacZ after treatment with T4 DNA polymerase, giving plasmid pΔMnlacz. pJ4lacZ was produced by insertion of the lacZ gene from pCH110 (Pharmacia) as a BamHI/HindIII fragment into the KpnI site of pJ4 (Morgenstern and Land, 1990) after treatment with T4 DNA polymerase.

Growth of Mutant HSV Strains Using Complementing Cell Lines

A complementing cell line (B130/2) allowing growth of ICP27 deleted viruses and having no overlap between the complementing sequences and the ICP27 deleted viruses above (and thus preventing repair of ICP27 by homologous recombination during virus growth) was generated by co-transfection of plasmid pSG130BS (Sekulovich et al., 1988) DNA with neomycin resistance-encoding plasmid pMamNeo (Invitrogen) into BHK cells and the selection of neomycin resistant clones. A clone highly permissive for the growth of an HSV-1 ICP27 deletion mutant (B130/2) was selected for virus growth. PSG130BS carries a BamHI/SacI fragment from HSVL (nts 113322–115743) encoding the complete ICP27 coding sequence and part of UL55, but has no overlap with pΔMN.

There have been no previously reported ICP27 deletion mutant cell-line combinations in which there is no overlap between the sequences inserted into the cell-line for complementation and sequences remaining in the virus, and thus preventing repair of ICP27 by homologous recombination. Low level reversion to a pathogenic phenotype has previously been reported for ICP4 deletion mutant/ICP4 expressing cell line combinations in which there has been overlap between the remaining viral and inserted sequences, and thus allowing repair of the ICP4 mutation by homologous recombination.

Results

Male Lewis rats were stereotaxically inoculated in the striatum with 1 μl of a $10^9$ pfu/ml stock of either HSV strains zΔMN:16 or zΔMN:+ described above, or 1 μl of a $10^9$ pfu/ml of HSV-1 strain 1716/pR9. A drawn out glass capillary was used for inoculation and the inoculum was introduced over a period of 5 mins. 1716/pR9, which has been described previously is strain 1716 (deleted for ICP34.5) with a lacZ gene inserted into the non-essential gene UL43. After 2 days rats were killed and sections stained for lacZ activity with X-gal. X-gal positive cells were counted in each case.

| Virus | 1716/pR9 | zΔMN:16 | zΔMN:+ |
|---|---|---|---|
| Average number of blue cells/ 75 μm section (5 sections counted). | 12 | 680 | 740 |

These results show that while deletion of ICP34.5 does not preclude expression of a heterologous gene, this deletion alone does not allow highly efficient gene transfer, although it does provide a virus with severely reduced pathogenicity. However the additional removal of the essential IE gene ICP27, requiring virus growth on an ICP27 expressing cell line, not only provides increased safety, due to the absolute block to a productive infection in any cell type in the absence of ICP27, and probable reduced cytotoxicity, it also highly significantly and unexpectedly increases the number of cells from which a heterologous gene can be expressed. Moreover this number of cells is not significantly reduced as compared to inoculation with a virus containing the ICP27 mutation alone (which is less safe because it is not deleted for ICP34.5).

The experiment using zΔMN:16 was repeated using stereotaxic inoculation to the striatum of two 3 month old common marmosets (*Callithrix jacchus*) giving very similar results to the experiments rat experiments. Here greater than 600 cells, many with neuronal morphology, stained blue with X-gal in each 75 μm section. Thus the results obtained with rats have been extended to more relevant models of human disease, in this case with a species often used as a model system for studying Parkinson's disease.

These results clearly show that while deletion of ICP34.5 from the HSV genome provides a non-neurovirulent phenotype, the efficiency of heterologous gene expression of such a mutant in the brain is poor. However in combination with deletion of ICP27, ICP34.5/ICP27 deletion mutants unexpectedly provided highly efficient gene transfer to the brain. This, in combination with the anticipated advantage of a high degree of added safety and probable reduced cytotoxicity when using the double mutant, suggests that HSV-1 ICP34.5/ICP27 deletion mutants are highly promising for further development as vectors for gene delivery to the nervous system.

Example 2
HSV Strains Defective in ICP34.5, ICP27 and VMW65

After infection by an ICP27/ICP34.5 double mutant, host cell metabolism will still be altered by the expression of a number of other HSV genes might be toxic in vivo. We thus further speculated that removal of further genes to minimise HSV gene expression would again improve the characteristics of the virus when used as a vector. To achieve this, an inactivating mutation was made in VMW65, the virion transcriptional activator protein, which is carried in the virion and is responsible for stimulating IE gene expression after infection (Ace et al., 1989). This mutation should greatly reduce the levels of ICP0 and the other IE genes ICP22 and 47. These VMW65 mutants need not additionally be complemented in culture by a functional VMW65 gene as they are grown at high multiplicity or by inclusion of hexamethylene-bisacetamide (HMBA) in the media (McFarlane et al., 1992).

Viruses

ICP34.5 deletion mutants with a mutation producing a functional inactivation of the transcriptional-activating activity of VMW65 were produced by co-cultivation (in BHK cells with 3 mM HMBA) of strain 1716, containing a deletion in both copies of ICP34.5 (MacLean et al., 1991), with strain in 1814 (Ace et al, 1989) containing a functionally inactivated VMW65 gene. The genomic structure of resultant plaques was analysed by methods known to those skilled in the art (restriction digestion of purified genomic DNA and Southern blotting) and virus containing both the in 1814 and 1716 mutations further plaque-purified five times, giving the virus strain 1764.

ICP27 was removed from strain 1764 using pΔMNlacZ and purified strain 1764 genomic DNA, as in Example 1 for the deletion of ICP27 from strain 1716, except with the inclusion of 3 mM HMBA in the media, giving strain zΔMN:64.

Results

HSV strain zΔMN:64 was tested both in vitro and in vivo as compared to the viruses described in Example 1. The results showed that, in vivo, similar numbers of blue X-gal staining cells were seen in brain sections 2 days after inoculating $1 \times 10^6$ pfu stereotaxically into the striatum of a male Lewis rat as for zΔMN:+ and zΔMN:16 (approximately 700 blue staining cells/75 μm section). However while the level of gene transfer was relatively similar between the three viruses, the degree of macrophage infiltration as assessed by electron microscopy was somewhat reduced in zΔMN:64 as compared to zΔMN:+ and ZΔMN:16 suggesting a lower degree of cytotoxicity and/or immunogenicity, possibly associated with the reduced HSV gene expression when using zΔMN:64.

In vitro these differences were more marked as primary cultures of enteric neurons (derived from 7 day old Sprague-Dawley rat guts—Saffrey et al., 1991) showed considerably enhanced survival (as assessed by trypan blue staining) and maintenance of neuronal morphology after 3 days in culture after treatment in a 96 well microtitre dish with $2 \times 10^6$ pfu/well of zΔMN:64 as compared to ZΔMN:+ or zΔMN:16. Thus 60–80% of cells maintained neuronal processes after 3 days with zΔMN:64 as compared to approximately 20% with ZΔMN:+ or zΔMN:16. However even with zΔMN:64, after 7 days the number of cells showing normal neuronal morphology was considerably reduced as compared to untreated cultures. Thus in this assay to assess toxicity zΔMN:64 showed enhanced characteristics as compared to zΔMN:+ and zΔMN:16 which also extends to the in vivo situation as described above.

Example 3
HSV Strains Defective in ICP34.5, ICP27, VMW65 and ICP4

However ICP4 levels are likely to be little reduced by the mutation in VMW65 and it is thus desirable to functionally inactivate ICP4 as well. Mutant HSV strains were therefore constructed that were additionally deleted for the ICP4 gene. Thus a further mutant HSV strain defective in ICP34.5, ICP27, ICP4 and VMW65 was produced. This strain should express only low levels of gene products, other than an inserted heterologous gene, in infected cells, as no HSV gene expression is stimulated by either VMW65, ICP27 or ICP4 and essentially none by ICP0 or ICP22.

Viruses

Both copies of ICP4 were removed from strain zΔMN:64 first by the removal of lacZ from the ICP27 locus. This was achieved by homologous recombination of purified strain zΔMN:64 genomic DNA with plasmid pΔMN into B1/30 cells, and selection of non-lacZ containing plaques by X-gal staining (white plaques) and Southern blotting, to confirm the removal of the entire lacZ gene, giving strain 1764/27⁻w. Nucleotide numbers refer to the HSV strain 17+ sequence (Genbank no. HE1CG). A plasmid allowing deletion of ICP4 (pΔICP4) was then constructed using ICP4 flanking sequences (nts 123,459–126,774 [Sau3aI—Sau3aI] and nts 131,730-134-792[SphI-KpnI] separated by XbaI and SalI sites derived from pSP72; Promega, in which the construct was made). An approximately 0.8 kb NotI fragment (nts 124,945–125,723) containing the coding region for ICP34.5 was also removed to prevent the repair of the ICP34.5 deletion during homologous recombination with 1764/27⁻w.

A chimeric LAT promoter (nts 118,866–120,221[PstI-BstXI]/CMV IE promoter (from pcDNA3 (Invitrogen))/lacZ (from pCH110; Pharmacia) cassette —the pR20 cassette— was then inserted at the unique XbaI site giving pΔICP4/pR20. This plasmid was then introduced into strain 1764/27⁻w by homologous recombination as before and lacZ expressing plaques identified by staining with X-gal and plaque purification on B4/27 cells (described below) complementing the mutations in both ICP4 and ICP27, giving virus strain 1764/27/4⁻/pR20. Plaque purified virus could not give a productive infection either on 1/30 cells (expressing ICP27 but not ICP4) or BHK cells (expressing neither ICP27 nor ICP4).

ICP27/ICP4 Double Complementing Cell Line

A complementing cell line (4/27) allowing growth of ICP27/ICP4 deleted viruses in which repair of the ICP27 or ICP4 deletions by homologous recombination is not possible was generated by co-transfection of plasmid pSG130BS (containing the ICP27 coding sequence and promoter; Sekulovich et al., 1988) with pICP4 (a DdeI-SphI fragment [nts 126,764–131,730] containing the ICP4 coding region and promoter cloned between the EcoRV and SphI sites of pSP72[Promega]) and pMamNeo (Invitrogen; encoding neomycin resistance) into BHK cells and selection of neomycin resistant clones. A clone highly permissive for growth of an ICP4 mutant and an ICP27 mutant was selected (B4/27).

There have been no previously reported ICP4/ICP27 deletion mutant/cell line combinations in which repair of the ICP4 or ICP27 by homologous recombination during virus growth is not possible.

Results

1764/27/4⁻/pR20 was tested in vivo as in Examples 1 and 2 and in vitro as in Example 2. In vitro results were similar to the results for zΔMN:64 except that neuronal morphology (presence of processes) was maintained until the end of the experiment (7 days), with no increase in cell death as compared to untreated controls. This demonstrated the reduced toxicity of this virus as compared to zΔMN:16 and zΔMN:64. These results suggest that these viruses are highly attenuated to a level such that effects on host cell physiology are minimal and suggest that any remaining toxicity in vivo is likely to be associated with immune responses to the virus particle after inoculation, and also immune responses to the high levels of expressed heterologous gene, in this case lacZ.

In vivo results in rats using $1 \times 10^6$ pfu of 1764/27/4⁻/pR20 inoculated as in Example 1, showed a similar number of cells transfected as with the other mutants zΔMN:+, zΔMN:16 and zΔMN:64 after 2 days, and from the in vitro data this can be expected to be associated with further reduced toxicity. In this case this reduced toxicity and/or immunogenicity was demonstrated by improved expression characteristics in the longer term. Thus here, using the promoter/lacZ combination described (pR20), which is different to that used in Examples 1 and 2 but unlike the MMLV LTR promoter is active during herpes latency (unpublished results), approximately 30% of the number of cells which stain blue with X-gal after 2 days stain blue after 1 month. This compares to approximately 5% of cells staining blue after 1 month as compared to 2 days when using an ICP27-only deleted virus with the pR20 promoter/lacZ cassette inserted into the ICP27 locus.

Example 4
HSV Strains Defective in Vhs

Thus, for strains mutated in ICP34.5, ICP27, ICP4 and VMW65, cell physiology will only be altered by proteins delivered to the cell in the virion and possibly by expression of ICP6 which can still be expressed as an IE gene. Of these virion proteins, most are structural proteins and the virion host shutoff protein (vhs). Vhs is responsible for the destabilisation of host mRNAS in favour of translation from more rapidly produced HSV mRNAS after infection (Reef Hardy and Sandri-Goldin, 1994), and is thus potentially highly cytotoxic. Thus a further modification may be made to the mutant HSV strains of the invention by the functional activation of vhs (which is unnecessary for growth in culture).

Vhs mutations have not been included in vectors previously reported as having been tested for gene delivery in vivo. The ICP27 and ICP4 deletions give no overlap between the virus and the complementing sequences in the double-expressing cell line (i.e. expressing ICP27 and ICP4) used preventing any reversion by homologous recombination, and the ICP34.5 mutation provides a final level of safety in the unlikely event that the ICP27 and ICP4 deletions should become repaired.

REFERENCES

Coffin R S, Latchman D S. Herpes simplex virus-based vectors. In: Latchman D S (ed). Genetic manipulation of the nervous system. Academic Press: London, 1996, pp 99–114.

MacLean A R et al. Herpes simplex virus type I deletion variants 1714 and 1716 pinpoint neurovirulence related sequences in Glasgow strain 17+between immediate early gene I and the 'a' sequence. J Gen Virol 1991; 72:632–639.

Shinnick T M et al. Nucleotide sequence of Moloney murine leukaemia virus. Nature 1981; 293:543–548.

Morgenstern J P, Land H. A series of mammalian expression vectors and characterisation of their expression of a reporter gene in stably and transiently transfected cells. NAR 1990.; 18:1068.

Sekulovich R E et al. J. Virot 1988; 64:3916–3926.

Ace C et al. Construction and characterisation of a herpes simplex virus type I mutant unable to transinduce immediate early gene expression. J Virol 1989; 63:2260–2269.

McFarlane M, Daksis J I, Preston C M. Hexamethylene bisacetamide stimulates herpes-simplex virus immediate early gene-expression in the absence of trans-induction by VMW65. J Gen Virol 1992; 73:285–292.

Schek N, Bachenheimer S L. Degradation of cellular mRNAs induced by a virion-associated factor during herpes simplex virus infection of Vero cells. J. Virol 1985; 55:601–610.

Rice, S A and Knipe D M. Genetic evidence for two distinct transactivation functions of the herpes simplex virus α protein ICP27. J. Virol 1990; 64:1704–1715.

Reef Hardy, W and Sandri-Goldin R M. Herpes simplex virus inhibits host cell splicing and regulatory protein ICP27 is required for this effect J. Virol 1994; 68:7790–7799.

Dobson, A T et al. A latent, non-pathogenic HSV-1-derived vector stably expresses β-galactosidase in mouse neurons. Neuron 1990; 5:353–360.

Chou, J., Kern, E R, Whitley, R J and Roizman, B. Mapping of herpes simplex virus-1 neurovirulence to $\gamma_1 34.5$, a gene nonessential for growth in culture. Science 1990; 250:1262–1266.

Chiocca, A E et al. Transfer and expression of the lacZ gene in rat brain neurons by herpes simplex virus mutants. New Biol. 1990; 2:739–736.

Chou, J. and Roizman, B. The $\gamma_1 34.5$ gene of herpes simplex virus 1 precludes neuroblastoma cells from triggering total shutoff of protein synthesis characteristic of programmed cell death in neuronal cells. PNAS 1992; 89:3266–3270.

Chou, J., Poon, A P W, Johnson, J. and Roizman B. Differential response of human cells to deletions and stop codons in the $\gamma_1 34.5$ gene of herpes simplex virus. J. Virol. 1994; 68:8304–8311.

Smith, I L, Hardwicke M A and Sandri-Goldin R M. Evidence that the herpes simplex virus immediate early protein ICP27 acts post-translationally during infection to regulate gene expression. Virology 1992; 186:74–86.

Samaniego L A et al. J. Virol. 1995; 69:5705–5715.

DeLuca N A et al. J. Virol. 1985; 56:558–570.

Lokensgard J R et al. J. Virol. 1994; 68:7148–7158.

Saffrey et al., cell and tissue culture research. 1991; 265:527–534.

What is claimed is:

1. A herpes simplex virus (HSV) which lacks a functional ICP34.5 gene and a functional ICP27 gene.

2. An HSV according to claim 1 which is selected from the group consisting of a mutant HSV-1, a mutant HSV-2 and a HSV-1/HSV-2 recombinant mutant.

3. The HSV according to claim 2 which carries a heterologous gene operably linked to a sequence that controls expression of said heterologous gene in mammalian cells.

4. An HSV according to claim 1 wherein the lack of a functional ICP34.5 gene is due to a deletion or insertion within said gene.

5. An HSV according to claim 1 wherein the lack of a functional ICP27 gene is due to a deletion or insertion within said gene.

6. An HSV according to claim 1 which further lacks a functional second IE gene other than ICP27.

7. An HSV according to claim 6 wherein said IE gene is ICP4.

8. The HSV according to claim 7 which carries a heterologous gene operably linked to a sequence that controls expression of said heterologous gene in mammalian cells.

9. A composition comprising an HSV according to claim 8 together with a carrier or diluent.

10. The HSV according to claim 6 which carries a heterologous gene operably linked to a sequence that controls expression of said heterologous gene in mammalian cells.

11. A composition comprising an HSV according to claim 10 together with a carrier or diluent.

12. An HSV according to claim 1 which further lacks a functional VMW65 gene due to a mutation in said gene which abolishes its transcriptional-activation activity.

13. The HSV according to claim 12 which further lacks a functional vhs gene.

14. The HSV according to claim 13 which carries a heterologous gene operably linked to a sequence that controls expression of said heterologous gene in mammalian cells.

15. A composition comprising an HSV according to claim 14 together with a carrier or diluent.

16. The HSV according to claim 12 which carries a heterologous gene operably linked to a sequence that controls expression of said heterologous gene in mammalian cells.

17. A composition comprising an HSV according to claim 16 together with a carrier or diluent.

18. An HSV according to claim 1 which further lacks a functional vhs gene.

19. The HSV according to claim 18 which carries a heterologous gene operably linked to a sequence that controls expression of said heterologous gene in mammalian cells.

20. A composition comprising an HSV according to claim 19 together with a carrier or diluent.

21. An HSV according to claim 1 which carries a heterologous gene.

22. An HSV according to claim 21 wherein said heterologous gene is operably linked to a sequence that controls expression of said heterologous gene in mammalian cells.

23. An HSV according to claim 22 wherein said mammalian cell is a cell of the central or peripheral nervous system of a mammal.

24. An HSV according to claim 21 wherein said heterologous gene encodes a polypeptide of therapeutic use.

25. An HSV according to claim 24 wherein said gene encodes a polypeptide which is cytotoxic.

26. An HSV according to claim 24 wherein said gene encodes a polypeptide that converts a precursor prodrug into a cytotoxic compound.

27. An HSV according to claim 22 wherein said mammalian cell is a cell of the eye, heart or skeletal muscle of a mammal.

28. An HSV according to claim 22 wherein the heterologous gene is selected from the group consisting of genes encoding proteins involved in the regulation of cell division, enzymes involved in metabolic pathways, transcription factors and heat shock proteins.

29. A composition comprising an HSV according to claim 22 together with a carrier or diluent.

30. A method for producing a herpes simplex virus according to claim 1 said method comprising modifying the ICP34.5 and ICP27 genes of a herpes simplex virus so as to functionally inactivate said genes.

* * * * *